United States Patent [19]

Kremer et al.

[11] Patent Number: 5,849,916

[45] Date of Patent: Dec. 15, 1998

[54] PROCESS FOR THE PREPARATION OF 2,3-PYRIDINEDICARBOXIMIDES

[75] Inventors: Kenneth Alfred Martin Kremer; Wen-Xue Wu, both of Lawrenceville; Donald Roy Maulding, deceased, late of Somerville, all of N.J., by Nancy Kay Maulding, executrix

[73] Assignee: American Cyanamid Company, Madison, N.J.

[21] Appl. No.: 872,568

[22] Filed: Jun. 10, 1997

Related U.S. Application Data

[60] Provisional application No. 60/019,511 Jun. 10, 1996.
[51] Int. Cl.[6] ...................... C07D 471/04; C07D 401/04
[52] U.S. Cl. .......................................... 546/113; 546/274.1
[58] Field of Search ............................................. 546/113

[56] References Cited

U.S. PATENT DOCUMENTS

| | | | |
|---|---|---|---|
| 4,748,244 | 5/1988 | Waldner et al. | 544/313 |
| 4,754,033 | 6/1988 | Waldner | 544/127 |
| 4,798,619 | 1/1989 | Los | 504/156 |
| 5,288,866 | 2/1994 | Strong | 544/215 |
| 5,334,576 | 8/1994 | Doehner, Jr. et al. | 504/128 |

FOREIGN PATENT DOCUMENTS 0 308 084-A1  8/1988  United Kingdom .

OTHER PUBLICATIONS

Sylvia J. Allcock, et al., Tetrahedron (1991) 47 No. 48.
Adrian Waldner, Helvetica Chimica Acta (1988) 71 No. 2, pp. 486–492 (Chem. Abst. 110:23757f, 1989).

*Primary Examiner*—Alan L. Rotman
*Attorney, Agent, or Firm*—Barbara L. Renda

[57] ABSTRACT

There is provided a process for the preparation of 2,3-pyridinedicarboximides having the structural formula I

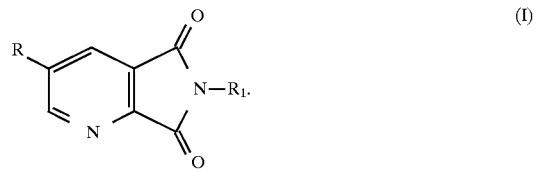

The 2,3-pyridinedicarboximides are useful as intermediates in the preparation of herbicidal 2-(2-imidazolin-2-yl)nicotinic acids, esters and salts.

15 Claims, No Drawings

PROCESS FOR THE PREPARATION OF 2,3-PYRIDINEDICARBOXIMIDES

This application claims priority from copending provisional application(s) Ser. No. 60/019,511 filed on Jun. 10, 1996.

BACKGROUND OF THE INVENTION 2,3-Pyridinedicarboximides are useful as intermediates in the preparation of herbicidal 2-(2-imidazolin-2-yl)nicotinic acids, esters and salts. Methods for the preparation of 2,3-pyridinedicarboximides are known in the art (see, e.g., U.S. Pat. No. 4,748,244; U.S. Pat. No. 4,754,033 and EP 308,084-A1). However, the methods described in those patents and patent application are not entirely satisfactory for the commercial manufacture of 2,3-pyridinedicarboximides.

It is, therefore, an object of the present invention to provide an effective and efficient process for the preparation of 2,3-pyridinedicarboximides.

It is also an object of the present invention to provide a compound which is useful in the process of this invention.

These and other objects and features of the present invention will become more apparent from the detailed description thereof set forth below.

SUMMARY OF THE INVENTION

The present invention provides an effective and efficient process for the preparation of a 2,3-pyridinedicarboximide having the structural formula I

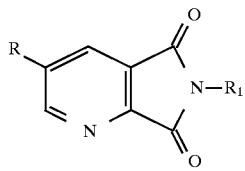

wherein
R is hydrogen, $C_1$–$C_6$alkyl or $C_1$–$C_6$alkoxymethyl;
$R_1$ is hydrogen, $C_1$–$C_6$alkyl, $C(O)R_2$,
    phenyl optionally substituted with any combination of from one to four halogen, $C_1$–$C_4$alkyl, $C_1$–$C_4$alkoxy, nitro or cyano groups,
    benzyl optionally substituted on the phenyl ring with any combination of from one to four halogen, $C_1$–$C_4$alkyl, $C_1$–$C_4$alkoxy, nitro or cyano groups, or

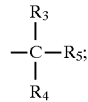

$R_2$ is $C_1$–$C_6$alkyl, benzyl or
    phenyl optionally substituted with any combination of from one to four halogen, $C_1$–$C_4$alkyl, $C_1$–$C_4$alkoxy, nitro or cyano groups;
$R_3$ and $R_4$ are each independently $C_1$–$C_4$alkyl; and
$R_5$ is cyano or $CONH_2$,
which process comprises reacting an oxime or hydrazone having the structural formula II

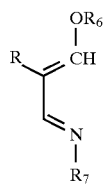

wherein
R is as described above;
$R_6$ is $C_1$–$C_6$alkyl;
$R_7$ is $OR_8$ or $NR_9R_{10}$;
$R_8$ is hydrogen, $C_1$–$C_6$alkyl, $C(O)R_{11}$,
    phenyl optionally substituted with any combination of from one to four halogen, $C_1$–$C_4$alkyl, $C_1$–$C_4$alkoxy, nitro or cyano groups, or
    benzyl optionally substituted on the phenyl ring with any combination of from one to four halogen, $C_1$–$C_4$alkyl, $C_1$–$C_4$alkoxy, nitro or cyano groups;
$R_{11}$ is $C_1$–$C_6$alkyl, $OR_{12}$, $NR_{12}R_{13}$, benzyl or
    phenyl optionally substituted with any combination of from one to four halogen, $C_1$–$C_4$alkyl, $C_1$–$C_4$alkoxy, nitro or cyano groups;
$R_{12}$ and $R_{13}$ are each independently hydrogen, $C_1$–$C_6$alkyl,
    benzyl or
    phenyl optionally substituted with any combination of from one to four halogen, $C_1$–$C_4$alkyl, $C_1$–$C_4$alkoxy, nitro or cyano groups; and
$R_9$ and $R_{10}$ are each independently hydrogen, $C_1$–$C_6$alkyl,
    benzyl or
    phenyl optionally substituted with any combination of from one to four halogen, $C_1$–$C_4$alkyl, $C_1$–$C_4$alkoxy, nitro or cyano groups,
with a maleimide having the structural formula III

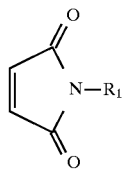

wherein $R_1$ is as described above.
This invention also relates to the formula II oximes described hereinabove.

DETAILED DESCRIPTION OF THE INVENTION

In one preferred embodiment of the present invention, an oxime or hydrazone represented by formula II is reacted with a maleimide represented by formula III, preferably in a temperature range of about 20° C. to 160° C., in the presence of a solvent.

Advantageously, it has now been found that 2,3-pyridinedicarboximides may be obtained in high yield and/or high purity by the effective and efficient process of the present invention.

The 2,3-pyridinedicarboximides may be isolated by diluting the reaction mixture with water and filtering the formula I product from the aqueous mixture. The product formula I compounds may also be isolated by concentrating the reaction mixture in vacuo and filtering the formula I product from the concentrated mixture. Alternatively, the reaction mixture may be integrated into the process used to prepare the final herbicidal agent without isolating the formula I compound.

Exemplary of halogen hereinabove are fluorine, chlorine, bromine and iodine.

In another embodiment of the present invention, a Lewis acid is present. Preferably, the Lewis acid is present in an amount up to about one molar equivalent relative to the formula II compound when $R_8$ is hydrogen. Lewis acids suitable for use in the present invention include any conventional Lewis acids. Preferred Lewis acids include aluminum chloride and titanium(IV) chloride.

Solvents suitable for use in the process of the present invention preferably have a boiling point of at least about 60° C. and include aromatic hydrocarbons such as toluene, xylenes, mesitylene and mixtures thereof; halogenated aromatic hydrocarbons such as mono—and dihalobenzenes and mixtures thereof; polynuclear aromatic hydrocarbons such as naphthalene, alkylnaphthalenes and mixtures thereof; ethers such as tetrahydrofuran and mixtures thereof; glycols such as 1,2-diethoxyethane and mixtures thereof; an alkanoic acid such as acetic acid, propionic acid and mixtures thereof; an alkanoic acid/water mixture such as an acetic acid/water mixture; acetonitrile; an acetonitrile/water mixture; and mixtures thereof. Preferred solvents include toluene, xylenes, mesitylene, acetonitrile, an acetonitrile/water mixture, acetic acid and mixtures thereof with toluene and acetonitrile being more preferred.

In another preferred embodiment of the present invention, oximes of formula II wherein $R_7$ is $OR_8$ are reacted with maleimides of formula III preferably at a temperature range of about 60° C. to 160° C., more preferably about 75° C. to 135° C. And hydrazones of formula II wherein $R_7$ is $NR_9R_{10}$ are reacted with maleimides of formula III preferably at a temperature range of about 20° C. to 160° C., more preferably about 20° C. to 135° C.

In a further preferred embodiment of the present invention, a base is present when R is $C_1$–$C6$alkoxymethyl. The base is used to reduce the amount of 5-methyl-2,3-pyridinedicarboximides which are produced as undesirable by-products when R is $C_1$–$C_6$alkoxymethyl.

Bases suitable for use in the present invention include, but are not limited to, tri($C_2$–$C_4$alkyl)amines such as triethylamine, N,N-diethylisopropylamine, N,N-diisopropylethylamine and the like, alkali metal acetates such as sodium acetate, potassium acetate and the like, and mixtures thereof. Preferred bases include triethylamine, sodium acetate and potassium acetate. The base is preferably present in an amount of at least about one molar equivalent relative to the formula II compound.

In a further embodiment of the present invention, a phase transfer catalyst is present when the base is present. Preferably, the phase transfer catalyst is present when the alkali metal acetate is present. Phase transfer catalysts suitable for use in the present invention include any conventional phase transfer catalysts. Preferred phase transfer catalysts include crown ethers such as 18-crown-6 and 15-crown-5.

In a preferred process of the present invention,

R is hydrogen, $C_1$–$C_4$alkyl or $C_1$–$C_4$alkoxymethyl;

$R_1$ is hydrogen, $C_1$–$C_4$alkyl,
  phenyl optionally substituted with any combination of from one to four halogen, $C_1$–$C_4$alkyl, $C_1$–$C_4$alkoxy, nitro or cyano groups, or

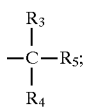

$R_3$ and $R_4$ are each independently $C_1$–$C_4$alkyl;

$R_5$ is cyano or $CONH_2$;

$R_6$ is $C_1$–$C_4$alkyl;

$R_7$ is $OR_8$; and $R_8$ is hydrogen or $C_1$–$C_6$alkyl.

In a more preferred process of the present invention,

R is hydrogen, methyl, ethyl or methoxymethyl;

$R_1$ is methyl, phenyl or

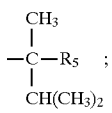

$R_5$ is cyano or $CONH_2$;

$R_6$ is methyl or ethyl;

$R_7$ is $OR_8$; and $R_8$ is hydrogen or methyl.

Formula II oximes wherein $R_7$ is $OR_8$; and $R_8$ is hydrogen, $C_1$–$C_6$alkyl,
  phenyl optionally substituted with any combination of from one to four halogen, $C_1$–$C_4$alkyl, $C_1$–$C_4$alkoxy, nitro or cyano groups, or
  benzyl optionally substituted on the phenyl ring with any combination of from one to four halogen, $C_1$–$C_4$alkyl, $C_1$–$C_4$alkoxy, nitro or cyano groups, may be prepared by reacting a 3-alkoxy-2-propenal of formula IV with a substituted hydroxylamine of formula V optionally in the presence of a base. The reaction scheme is shown below in Flow Diagram I.

FLOW DIAGRAM I

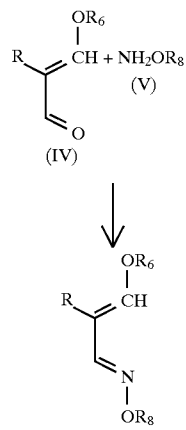

Alternatively, oximes of formula II wherein $R_8$ is $C_1$–$C_6$alkyl may be prepared by reacting a formula II compound wherein $R_8$ is hydrogen with a dialkyl sulfate of formula VI in the presence of a base such as sodium hydroxide or an alkali metal alkoxide. The reaction scheme is shown in Flow Diagram II.

FLOW DIAGRAM II

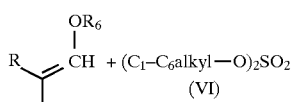

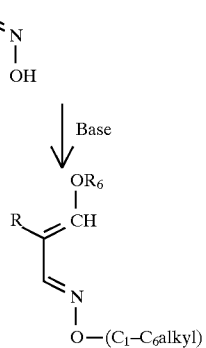

Formula II oximes wherein $R_8$ is $C(O)R_{11}$ may be prepared by reacting a formula II compound wherein $R_8$ is hydrogen with an acid chloride of formula VII or an anhydride of formula VIII as shown in Flow Diagram III.

FLOW DIAGRAM III

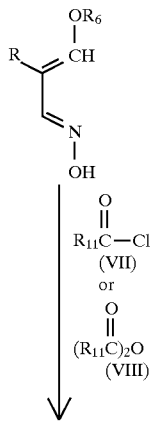

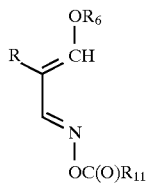

Formula II hydrazones may be prepared by reacting a 3-alkoxy-2-propenal of formula IV with a hydrazine of formula IX optionally in the presence of an acid catalyst such as acetic acid. The reaction scheme is shown in Flow Diagram IV.

FLOW DIAGRAM IV

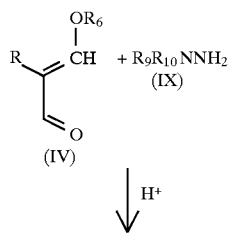

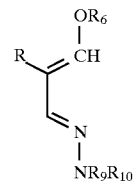

3-Alkoxy-2-propenal compounds of formula IV may be prepared according to the procedures described by E. Breitmaier, et al in *Synthesis*, pages 1–9 (1987). Maleimide compounds of formula III are known in the art and may be prepared according to the procedures described by M. Cava, et al in *Organic Synthesis*, 41, page 93 (1961).

Alternatively, formula IV compounds wherein R is methoxymethyl may be prepared by reacting a 3-(dialkyl-amino)-2-propenal of formula X with formaldehyde and methanol in the presence of a mineral acid such as sulfuric acid to form a 3-(dialkylamino)-2-(methoxy-methyl)-2-propenal of formula XI, and reacting the formula XI compound with a base such as an alkali metal hydroxide and a dialkyl sulfate of formula VI. The reaction scheme is shown in Flow Diagram V.

FLOW DIAGRAM V

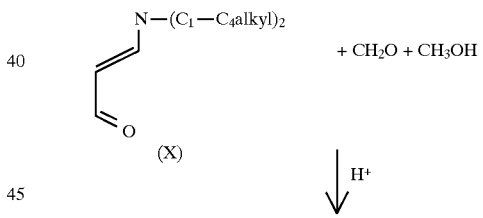

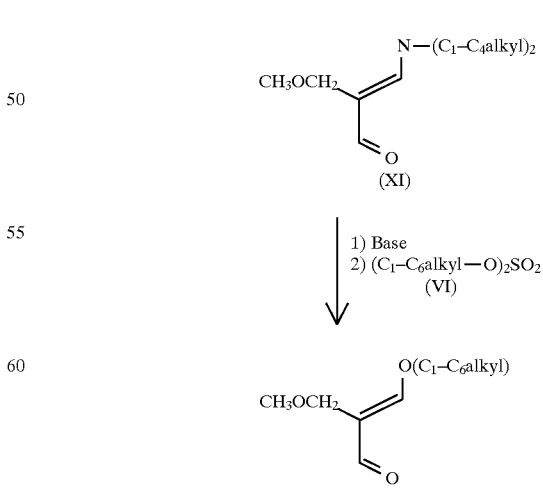

The present invention also provides a process for the preparation of a herbicidal 5-(alkoxymethyl)-2-(2-imidazolin-2-yl)-nicotinic acid, ester and salt compound having the formula

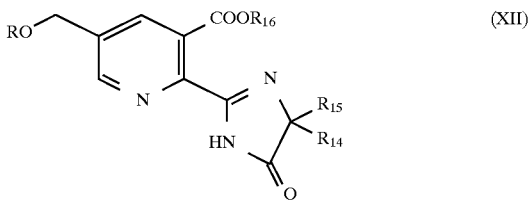
(XII)

wherein
R is as defined above;
$R_{14}$ is $C_1$–$C_4$ alkyl;
$R_{15}$ is $C_1$–$C_4$ alkyl, $C_3$–$C_6$ cycloalkyl or $R_{14}$ and $R_{15}$ when taken together with the atom to which they are attached, represent a $C_3$–$C_6$ cycloalkyl group optionally substituted with methyl and
$R_{16}$ is hydrogen, diloweralkylimino,
$C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, halophenyl, lower alkylphenyl, lower alkoxyphenyl, nitrophenyl, carboxyl, loweralkoxycarbonyl, cyano or triloweralkylammonium;
$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;
$C_3$–$C_6$ cycloalkyl optionally substituted with one or two $C_1$–$C_3$ alkyl groups; or
a cation preferably selected from the group consisting of alkali metals, alkaline earth metals, manganese, copper, iron, zinc, cobalt, lead, silver, nickel, ammonium and organic ammonium;
which process comprises:
(a) preparing a compound having the formula I

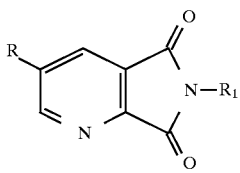
(I)

wherein R and $R_1$ are as defined above by a process as defined above; and
(b) converting the compound having formula I into the compound having the formula XII.

The term "lower" as used above in relation to alkyl and alkoxy groups means that the alkyl or alkoxy group contains 1 to 6, preferably 1 to 4, carbon atoms.

The conversion of the compound having formula I into the compound having formula XII may be carried out in a variety of ways. One may plan routes by combining reactions known for the conversion of one carboxylic acid derivative into another.

Methods that may be used to create the imidazolinone herbicides are illustrated in the book "The Imidazolinone Herbicides" edited by D. L. Shaner and S. L. O'Connor, published 1991 by CRC Press, Boca Raton, Fla. with particular reference to Chapter 2 entitled "Synthesis of the Imidazolinone Herbicides", pages 8–14 and the references cited therein. The following patent literature references also illustrate the methods that may be used to convert the carboxylic acid derivatives into imidazolinone final products:

U.S. Pat. Nos. 5,371,229; 5,334,576; 5,250,694; 5,276,157; 5,110,930; 5,122,608; 5,206,368; 4,925,944; 4,921,961; 4,959,476; 5,103,009; 4,816,588; 4,748,244; 4,754,033; 4,757,146; 4,798,619; 4,766,218; 5,001,254; 5,021,078; 4,723,011; 4,709,036; 4,658,030; 4,608,079; 4,719,303; 4,562,257; 4,518,780; 4,474,962; 4,623,726; 4,750,978; 4,638,068; 4,439,607; 4,459,408; 4,459,409; 4,460,776; 4,125,727 and 4,758,667, and European Patent Application Nos. EP-A-0-041,623 and EP-A-0-308,084.

In order to facilitate a further understanding of the invention, the following examples are presented primarily for the purpose of illustrating more specific details thereof. The invention should not be deemed limited by the examples as the full scope of the invention is defined in the claims.

EXAMPLE 1

Preparation of the Oxime of 3-ethoxy-2-methyl-2-propen-1-one, (E)— and (Z)—

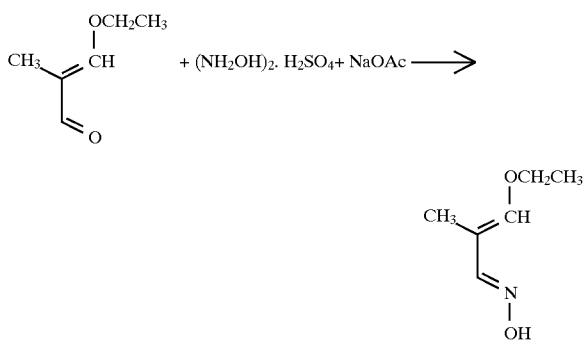

3-Ethoxy-2-methyl-2-propenal, (E)— and (Z)— (30.0 g, 0.25 mol) is added dropwise to a mixture of hydroxylamine sulfate (33.0 g, 0.2 mol) and sodium acetate (33.4 g, 0.4 mol) in water (200 g). The resultant reaction mixture is stirred overnight and filtered to obtain a solid. The solid is washed with water and dried to give the title product as a white solid (23.2 g, mp 78° C., 71% yield).

Using essentially the same procedure, but substituting methoxylamine hydrochloride for hydroxylamine sulfate, the O-methyloxime of 3-ethoxy-2-methyl-2-propen-1-one, (E)— and (Z)— is obtained as a yellow oil.

EXAMPLE 2

Preparation of the O-methyloxime of 3-ethoxy-2-methyl-2-propen-1-one, (E)— and (Z)—

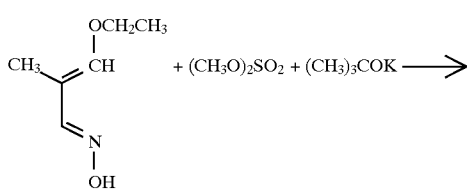

-continued

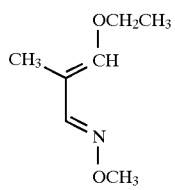

A mixture of the oxime of 3-ethoxy-2-methyl-2-propen-1-one, (E)— and (Z)— (0.5 g, 3.87 mmol) and potassium tert-butoxide (0.48 g, 4.2 mmol) in tetrahydrofuran is stirred for ten minutes at 10° C., treated dropwise with dimethyl sulfate (0.59 g, 4.6 mmol), stirred for two hours and filtered. The resultant filtrate is concentrated in vacuo to give the title product as a yellow oil (0.74 g, 100% yield).

EXAMPLE 3

Preparation of 5-Methyl-N-phenyl-2,3-pyridinedicarboximide

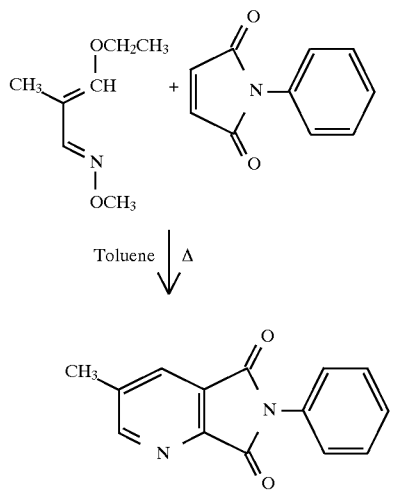

A solution of N-phenylmaleimide (1.69 g, 9.8 mmol) in toluene (16 g) is refluxed for 24 hours. During the reflux period, the O-methyloxime of 3-ethoxy-2-methyl-2-propen-1-one, (E)— and (Z)— (1.57 g, 11 mmol) is added portionwise to the reaction mixture. The final reaction mixture is then concentrated in vacuo to give the title product as a orange solid (1.2 g, 52% yield).

EXAMPLES 4–7

Using essentially the same procedure as described in Example 3, but substituting the oxime of 3-ethoxy-2-methyl-2-propen-1-one, (E)— and (Z)— for the O-methyloxime of 3-ethoxy-2-methyl-2-propen-1-one, (E)— and (Z)—, 5-methyl-N-phenyl-2,3-pyridinedicarboximide is produced in the yields shown in Table I.

TABLE I

Preparation of 5-Methyl-N-phenyl-2,3-pyridinedicarboximide

| Example | Equivalents of N-phenyl-maleimide | Lewis Acid/ Equivalents | Solvent | Hours Refluxed | % Yield |
|---|---|---|---|---|---|
| 4 | 0.3 | AlCl$_3$/0.2 | Toluene | 27 | 20 |
| 5 | 0.3 | TiCl$_4$/0.3 | Toluene | 10 | 10 |
| 6 | 0.2 | — | H$_2$O/CH$_3$CN (1:1) | 12 | 15 |
| 7 | 2.0 | — | CH$_3$CO$_2$H | 9 | 15 |

EXAMPLE 8

Preparation of 3-(Dimethylamino)-2-(methoxymethyl)-2-propenal, (E)— and (Z)—

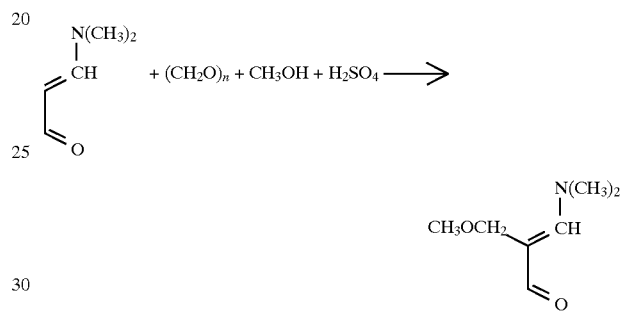

Concentrated sulfuric acid (1 mL) is slowly added to a solution of 3-(dimethylamino)-2-propenal (200 g, 2.01 mol) and paraformaldehyde (90 g, 3 mol) in methanol (1 L). The resultant solution is refluxed overnight, concentrated in vacuo to a volume of 200 mL, diluted with toluene and distilled until the vapor temperature is 105° C. The solution is then concentrated in vacuo to give the title product as an orange oil (251.4 g, 87% yield).

EXAMPLE 9

Preparation of 3-Methoxy-2-(methoxymethyl)-2-propenal, (E)— and (Z)—

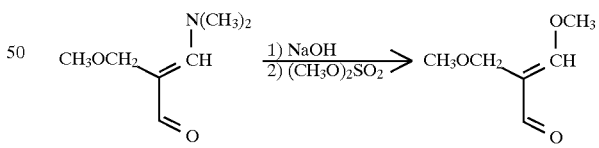

A solution of 3-(dimethylamino)-2-(methoxymethyl)-2-propenal, (E)— and (Z)— (53.06 g, 0.37 mol) and sodium hydroxide solution (29.7 g, 50%, 0.37 mol) in methanol (60 mL) is refluxed for 20 minutes and concentrated in vacuo to obtain a white solid. A solution of the solid in water (250 mL) is treated dropwise with dimethyl sulfate (46.75 g, 0.37 mol), stirred at room temperature for one hour and extracted with methylene chloride. The organic extract is dried over anhydrous sodium sulfate, concentrated in vacuo and distilled to give the title product as a colorless liquid (19.66 g, bp 80° C./0.5 mm Hg, 41% yield).

EXAMPLE 10

Preparation of 5-(Methoxymethyl)-N-phenyl-2,3-pyridinedicarboximide

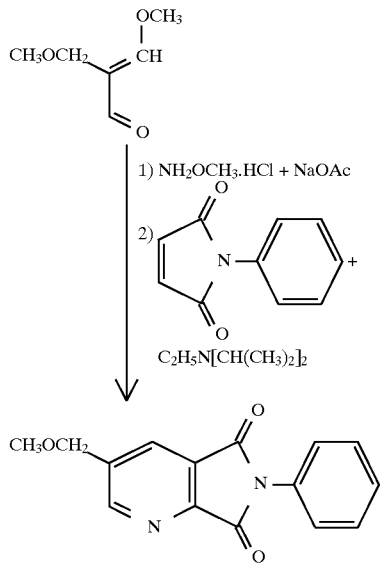

A solution of methoxyamine hydrochloride (1.7 g, 20 mmol) and sodium acetate (2.1 g, 25.6 mmol) in water (30 mL) is treated dropwise with 3-methoxy-2-(methoxymethyl)-2-propenal, (E)— and (Z)— (2.2 g, 16.9 mmol), stirred at room temperature for 30 minutes and extracted with methylene chloride. The organic extract is dried over anhydrous sodium sulfate and concentrated in vacuo to obtain the O-methyloxime of 3-methoxy-2-(methoxymethyl)-2-propen-1-one. A mixture of the resultant O-methyloxime of 3-methoxy-2-(methoxymethyl)-2-propen-1-one, N-phenylmaleimide (2.9 g, 16.8 mmol) and diisopropylethylamine (2.2 g, 17.0 mmol) in toluene (50 mL) is refluxed for 23 hours. During the reflux period, additional N-phenylmaleimide (2.9 g, 16.8 mmol) is added to the reaction mixture. The final reaction mixture is concentrated in vacuo to give the title product as a solid (0.36 g, 8% yield) having a 5-(methoxymethyl)-N-phenyl-2,3-pyridinedicarboximide to 5-methyl-N-phenyl-2,3-pyridinedicarboximide ratio of 50:1.

EXAMPLE 11

Preparation of 3-Ethoxy-2-methylacrolein dimethylhydrazone, (E)— and (Z)—

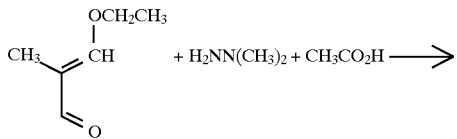

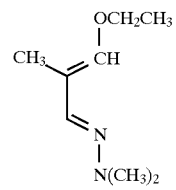

A mixture of 3-ethoxy-2-methyl-2-propenal, (E)— and (Z)— (4.0 g, 35 mmol), 1,1-dimethylhydrazine (2.73 g, 46 mmol) and acetic acid (0.04 g, 0.7 mmol) in diethyl ether is refluxed for one hour, cooled, washed sequentially with water and brine, dried over anhydrous magnesium sulfate, and concentrated in vacuo to give the title product as a yellow oil.

EXAMPLE 12

Preparation of 5-Methyl-N-phenyl-2,3-pyridinedicarboximide from N-phenylmaleimide and 3-ethoxy-2-methylacrolein dimethylhydrazone, (E)— and (Z)—

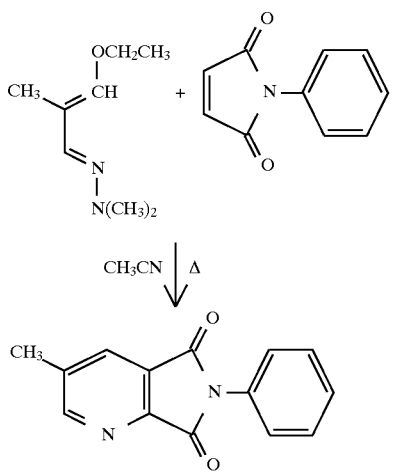

A solution of N-phenylmaleimide (1.1 g, 6.4 mmol) in acetonitrile is refluxed for 19 hours. During the reflux period, 3-ethoxy-2-methylacrolein dimethylhydrazone, (E)— and (Z)— (1.2 g, 7.6 mmol) is added portionwise to the reaction mixture. The final reaction mixture is then concentrated in vacuo to give the title product as a dark oil (0.23 g, 15% yield).

We claim:

1. A process for the preparation of a 2,3-pyridinedicarboximide having the structural formula I

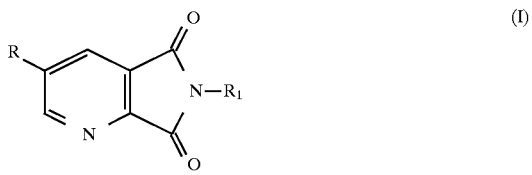

wherein

R is hydrogen, $C_1$–$C_6$alkyl or $C_1$–$C_6$alkoxymethyl;

$R_1$ is hydrogen, $C_1$–$C_6$alkyl, $C(O)R_2$, phenyl optionally substituted with any combination of from one to four halogen, or one to two $C_1$–$C_4$alkyl, $C_1$–$C_4$alkoxy, nitro or cyano groups, benzyl optionally substituted on the phenyl ring with any combination of from one to four halogen, or one to two $C_1$–$C_4$alkyl, $C_1$–$C_4$alkoxy, nitro or cyano groups, or

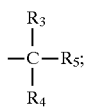

$R_2$ is $C_1$–$C_6$alkyl, benzyl or
  phenyl optionally substituted with any combination of from one to four halogen, or one to two $C_1$–$C_4$alkyl, $C_1$–$C_4$alkoxy, nitro or cyano groups;
$R_3$ and $R_4$ are each independently $C_1$–$C_4$alkyl; and
$R_5$ is cyano or $CONH_2$, which process comprises reacting an oxime or hydrazone having the structural formula II

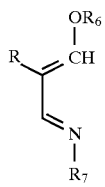

wherein
R is as described above;
$R_6$ is $C_1$–$C_6$alkyl;
$R_7$ is $OR_8$ or $NR_9R_{10}$;
$R_8$ is hydrogen, $C_1$–$C_6$alkyl, $C(O)R_{11}$,
  phenyl optionally substituted with any combination of from one to four halogen, or one to two $C_1$–$C_4$alkyl, $C_1$–$C_4$alkoxy, nitro or cyano groups, or
  benzyl optionally substituted on the phenyl ring with any combination of from one to four halogen, or one to two $C_1$–$C_4$alkyl, $C_1$–$C_4$alkoxy, nitro or cyano groups;
$R_{11}$ is $C_1$–$C_6$alkyl, $OR_{12}$, $NR_{12}R_{13}$, benzyl or
  phenyl optionally substituted with any combination of from one to four halogen, or one to two $C_1$–$C_4$alkyl, $C_1$–$C_4$alkoxy, nitro or cyano groups;
$R_{12}$ and $R_{13}$ are each independently hydrogen, $C_1$–$C_6$alkyl,
  benzyl or
  phenyl optionally substituted with any combination of from one to four halogen, or one to two $C_1$–$C_4$alkyl, $C_1$–$C_4$alkoxy, nitro or cyano groups; and
$R_9$ and $R_{10}$ are each independently hydrogen, $C_1$–$C_6$alkyl, benzyl or
  phenyl optionally substituted with any combination of from one to four halogen, or one to two $C_1$–$C_4$alkyl, $C_1$–$C_4$alkoxy, nitro or cyano groups,
with a maleimide having the structural formula III

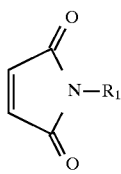

wherein $R_1$ is as described above.

2. The process according to claim 1 wherein
R is hydrogen, $C_1$–$C_4$alkyl or $C_1$–$C_4$alkoxymethyl;
$R_1$ is hydrogen, $C_1$–$C_4$alkyl, phenyl optionally substituted with any combination
  of from one to four halogen, $C_1$–$C_4$alkyl, $C_1$–$C_4$alkoxy, nitro or cyano groups, or

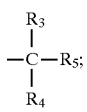

$R_6$ is $C_1$–$C_4$alkyl;
$R_7$ is $OR_8$; and
$R_8$ is hydrogen or $C_1$–$C_6$alkyl.

3. The process according to claim 2 wherein
R is hydrogen, methyl, ethyl or methoxymethyl;
$R_1$ is methyl, phenyl or

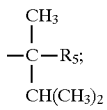

$R_6$ is methyl or ethyl; and
$R_8$ is hydrogen or methyl.

4. The process according to claim 1 wherein the formula II oxime or hydrazone is reacted with the formula III maleimide in the presence of a solvent.

5. The process according to claim 2 wherein the solvent is selected from the group consisting of an aromatic hydrocarbon, a halogenated aromatic hydrocarbon, a polynuclear aromatic hydrocarbon, a glycol, an alkanoic acid, an alkanoic acid/water mixture, acetonitrile, an acetonitrile/water mixture, and mixtures thereof, and the boiling point of the solvent is at least about 60° C.

6. The process according to claim 5 wherein the solvent is selected from the group consisting of toluene, a xylene, mesitylene, acetonitrile, an acetonitrile/water mixture, acetic acid and mixtures thereof.

7. The process according to claim 6 wherein the solvent is toluene or acetonitrile.

8. The process according to claim 1 wherein the formula II oxime is reacted with the formula III maleimide at a temperature of about 60° C. to 160° C.

9. The process according to claim 8 wherein the temperature is about 75° C. to 135° C.

10. The process according to claim 1 wherein the formula II hydrazone is reacted with the formula III maleimide at a temperature of about 20° C. to 160° C.

11. The process according to claim 10 wherein the temperature is about 20° C. to 135° C.

12. The process according to claim 1 further comprising a Lewis acid.

13. The process according to claim 12 wherein the Lewis acid is aluminum chloride or titanium(IV) chloride.

14. The process according to claim 1 further comprising a base when R is $C_1$–$C_6$alkoxymethyl.

15. The process according to claim 14 wherein the base is selected from the group consisting of a tri($C_2$–$C_4$alkyl) amine, an alkali metal acetate and mixtures thereof.

* * * * *